US005807557A

United States Patent [19]

Dubin

[11] Patent Number: 5,807,557
[45] Date of Patent: Sep. 15, 1998

[54] SOLUBLE HERPESVIRUS GLYCOPROTEIN COMPLEX

[75] Inventor: Gary Dubin, West Chester, Pa.

[73] Assignee: The Trustees of the University of Pennsylvania, Philadelphia, Pa.

[21] Appl. No.: 280,442

[22] Filed: Jul. 25, 1994

[51] Int. Cl.⁶ .......................... A61K 39/245; C12N 5/10; C12N 15/00
[52] U.S. Cl. ...................... 424/231.1; 435/325; 435/356; 435/172.3; 435/235.1; 435/69.3
[58] Field of Search ........................... 424/196.11, 229.1, 424/230.1, 231.1; 530/350; 435/69.1, 69.3, 172.3, 235.1, 240.2, 325, 326; 935/65

[56] References Cited

U.S. PATENT DOCUMENTS

| 4,291,019 | 9/1981 | Lupton et al. |
| 4,661,349 | 4/1987 | Kino et al. |
| 4,689,225 | 8/1987 | Pereira |
| 5,149,529 | 9/1992 | Ho et al. |
| 5,244,792 | 9/1993 | Burke et al. |
| 5,474,914 | 12/1995 | Spaete ..................................... 435/69.1 |

FOREIGN PATENT DOCUMENTS

| WO 89/07615 | 8/1989 | WIPO. |
| WO 89/10965 | 11/1989 | WIPO. |
| WO 90/11302 | 10/1990 | WIPO. |
| WO 91/02004 | 2/1991 | WIPO. |
| WO 92/01057 | 1/1992 | WIPO. |
| WO 92/05263 | 4/1992 | WIPO. |
| WO 94/21807 | 9/1994 | WIPO. |

OTHER PUBLICATIONS

Browne, H. et al. 1993, Journal of General Virology, vol. 74, pp. 2813–2817.
Spaete, R.R. et al. 1993. Virolog, vol. 193, pp. 853–861.
Yaswen, L.R. et al. 1993. Virology, vol. 195, pp. 387–396.
Hutchinson, L. et al. 1992. Journal of Virology, vol. 66, pp. 2240–2250.
Liu, D.X. et al. 1993. Journal of General Virology, vol. 74, pp. 1847–1857.
Liu, D.X. et al. 1993. Virology, vol. 197, pp. 12–22.
Andersson et al., "Cloning Structure, and Expression of the Mitochondrial Cytochrome P–450 Sterol 26–Hydroxylase, a Bile Acid Biosynthetic Enzyme." The Journal of Biological Chemistry, 264:8222–8229, 1989.
Blochlinger et al., "Hygromycin B Phosphotransferase as a Selectable Marker for DNA Transfer Experiments with Higher Eucaryotic Cells." Molecular and Cellular Biology, 4:2929–2931, 1984.
Cines et al., "Fc and C3 Receptors Induced by Herpes Simplex Virus on Cultured Human Endothelial Cells." J. Clin. Invest., 69:123–128, 1982.
Cohen at al., "Localization of Discontinuous Epitopes of Herpes Simplex Virus Glycoprotein D: Use of a Nondenaturing (Native Gel) System of Polyacrylamide Gel Electrophoresis Coupled with Western Blotting." Journal of Virology, 60:157–166, 1986.

Cranage et al., "Identification and Expression of a Human Cytomegalovirus Glycoprotein with Homology to the Epstein–Barr Virus BXLF2 Product, Varicella–Zoster Virus gpIII, and Herpes Simplex Virus Type 1 Glycoprotein H." Journal of Virology, 62:1416–1422, 1988.
Davison et al., "The Complete DNA Sequence of Varicella–Zoster Virus." J. Gen. Virol., 67:1759–1816, 1986.
Desai et al., "Excretion of Non–infectious Virus Particles Lacking Glycoprotein H by a Temperature–sensitive Mutant of Herpes Simplex Virus Type 1: Evidence that gH is Essential for Virion Infectivity." J. Gen Virol, 69:1147–1156, 1988.
Foa–Tomasi et al., "Herpes Simplex (HSV) Glycoprotein H is Partially Processed in a Cell Line that Expresses the Glycoprotein and Fully Processed in Cells Infected with Deletion or ts Mutants in the Known HSV Glycoproteins." Virology, 180:474–482, 1991.
Forrester et al., "Construction and Properties of a Mutant of Herpes Simplex Virus Type 1 with Glycoprotein H Coding Sequences Deleted." Journal of Virology, 66:341–348, 1992.
Friedman et al., "Use of a Glucocorticoid–Inducible Promoter for Expression of Herpes Simplex Virus Type 1 Glycoprotein gCL, a Cytotoxic Protein in Mammalian Cells." Molecular and Cellular Biology, 9:2303–2314, 1989.
Fuller et al., "Neutralizing Antibodies Specific for Glycoprotein H of Herpes Simplex Virus Permit Viral Attachment to Cells but Prevent Penetration." Journal of Virology, 63:3435–3443, 1989.
Gompels et al., "The Properties and Sequence of Glycoprotein H of Herpes Simplex Virus Type 1." Virology, 153:230–247, 1986.
Gompels et al., "Conservation of Glycoprotein H (gH) in Herpesviruses: Nucleotide Sequence of the gH Gene from Herpesvirus Saimiri." J. Virol, 69:2819–2829, 1988.
Gompels et al., "Antigenic Properties and Cellular Localization of Herpes Simplex Virus Glycoprotein H Synthesized in a Mammalian Cell Expression System." Journal of Virology, 63:4744–4755, 1989.
Graham et al., "A New Technique for the Assay of Infectivity of Human Adenovirus 5 DNA." Virology, 52:456–467, 1973.
Josephs et al., "Identification of the Hyman Herpesvirus 6 Glycoprotein H and Putative Large Tegument Protein Genes." Journal of Virology, 65(10):5597–5604, 1991.

(List continued on next page.)

Primary Examiner—Mary E. Mosher
Attorney, Agent, or Firm—Panitch Schwarze Jacobs & Nadel, P.C.

[57] ABSTRACT

The invention features a preparation of a soluble herpesvirus gH/gL complex, a cell encoding a soluble herpesvirus gH/gL complex, a vaccine comprising the complex and a method of immunizing a human against a herpesvirus infection using the complex. The invention further features a method of identifying antiviral compounds using a soluble herpesvirus gH/gL complex.

4 Claims, 11 Drawing Sheets (4 of 11 Drawing(s) Filed in Color)

OTHER PUBLICATIONS

Kaye et al., "Glycoprotein H of Human Cytomegalovirus (HCMV) Forms a Stable Complex with the HCMV UL115 Gene Product." Journal of General Virology, 73:2693–2698, 1992.

Klupp et al., "Sequence and Expression of the Glycoprotein gH Gene of Pseudorabies Virus." Virology, 182:732–741, 1991.

McGeoch et al., "DNA Sequence of the Herpes Simplex Virus Type 1 Gene Encoding Glycoprotein gH, and Identification of Homologues in the Genomes of Varicella–Zoster and Epstein–Barr Virus." Nucleic Acids Research, 14:4281–4292, 1986.

McGeoch et al., "The Complete DNA Sequence of the Long Unique Region in the Genome of Herpes Simplex Virus Type 1." J. Gen. Virol., 69:1531–1574, 1988.

Peeters et al., "Glycoprotein H of Pseudorabies Virus is Essential for Entry and Cell–To–Cell Spread of the Virus." Journal of Virology, 66:3888–3892, 1992.

Showalter, et al., "Monoclonal Antibodies to Herpes Simplex Virus Type 1 Proteins, Including the Immediate–Early Protein ICP4." Infection and Immunity, 34:684–692, 1981.

White, "Membrane Fusion.", Science, (Articles) 258:917–924, 1992.

Ghiasi et al., "Expression of Seven Herpes Simplex Virus Type 1 Glycoproteins (gB, gC, gD, gE, gG, gH, and gI): Comparative Protection Against Lethal Challenge in Mice", (1994) J. Virol. 68–4:2118–2126.

Roop et al., "A Mutant Herpes Simplex Virus Type 1 Unable to Express Glycoprotein L Cannot Enter Cells, and its Particles Lack Glycoprotein H", (1993) J. Virol. 67–4:2285–2297.

Ghiasi et al., "Baculovirus–Expressed Glycoprotein H of Herpes Simplex Virus Type 1 (HSV–1) Induces Neutralizing Antibody and Delayed Type Hypersensitivity Responses, but does not Protect Immunized Mice Against Lethal HSV–1 Challenge", (1992) J. Gen. Virol. 73:719–722.

Gompels et al., "Characterization and Sequence Analyses of Antibody–Selected Antigenic Variants of Herpes Simplex Virus Show a Conformationally Complex Epitope on Glycoprotein H", (1991) J. Virol. 65–5: 2393–2401.

Ghiasi et al., "Cell Surface Expression of Herpes Simplex Virus Type 1 Glycoprotein H in Recombinant Baculovirus–Infected Cells", (1991) Virology 185: 187–194.

Roberts et al., "Analysis of the Intracellular Maturation of the Herpes Simplex Virus Type 1 Glycoprotein gH in Infected and Transfected Cells", (1991) Virology 184: 609–624.

Buckmaster et al., "Characterisation and Physical Mapping of an HSV–1 Glycoprotein of Approximately $115 \times 10^3$ Molecular Weight", (1984) Virology 139: 408–413.

Mester, J.C. et al. 1991. Reviews of Infectious Diseases, vol. 13 (Suppl. 1), pp. S935–S945.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:1:

TGCTCTAGAG CGCTATGGGG ATTTTGGGT      29

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:2:

TGCTCTAGAG GTTTCCGTCG AGGCATCGT      29

SOLUBLE HERPESVIRUS GLYCOPROTEIN COMPLEX

FIELD OF THE INVENTION

This invention is directed to herpesvirus vaccines.

BACKGROUND OF THE INVENTION

Herpesviruses are ubiquitous viruses which are the causative agents of numerous diseases in both humans and animals. These viruses are enveloped double stranded icosahedral DNA containing viruses, which envelope is acquired by budding of the nucleocapsid through the inner nuclear membrane. Members of the herpesvirus family which are important human pathogens include herpes simplex virus type 1 (HSV-1), herpes simplex virus type 2 (HSV-2), varicella zoster virus (VZV), Epstein Barr virus (EBV), cytomegalovirus (CMV), and human herpesviruses type 6 and type 7 (HHV-6 and HHV-7).

The genome of HSV-1 encodes several glycoproteins which are important for viral pathogenesis. Four glycoproteins glycoprotein B (gB), glycoprotein D (gD), glycoprotein H (gH) and glycoprotein L (gL) are essential for virus infectivity in cells in culture and each appears to play a role in the mechanism by which the virus enters cells (Roop et al., 1993, J. Virol. 67:2285). Glycoprotein H is a 110 kDa protein encoded by the UL22 open reading frame of HSV-1 (Gompels and Minson, 1986, Virology 153:230). When gH is expressed in mammalian cell systems in the absence of other HSV-1 proteins it remains within the cell as an incompletely processed molecule (Foa-Tomasi et al., 1991, Virology 180:474; Roberts et al., 1991, Virology 184:609). When gH is expressed in cells which also express gL, gH and gL form a stable complex wherein fully processed gH is evident (Hutchinson et al., 1992, J. Virol. 66:2240). In addition, cells infected with a gL-negative mutant produce virus particles which lack both gH and gL (Roop et al., 1993, J. Virol. 67:2285). However, since transport of gH to the surface of cells is reported to occur in the absence of gL, gL may not be required in some systems for correct processing and transport of gH (Ghiasi et al., 1991, Virology 185:187).

A recombinant vaccinia virus expressing both gH and gL has been used to examine whether the gH/gL complex was capable of eliciting a protective immune response in mice. Weak levels of HSV-1 specific neutralizing antibody were evident in mice containing the complex and virus clearance from the site of challenge was only marginally enhanced when the gH/gL complex was administered to the animals compared with administration of gH alone (Browne et al., 1993, J. Gen. Virol. 74:2813).

Currently, there are no effective herpesvirus vaccines available for immunization of humans against any of the plethora of diseases caused by these pathogens, although subunit preparations comprising glycoprotein B, glycoprotein D, either alone or in combination are currently in clinical trials. Since herpesviruses cause recurrent and frequently fatal or permanently debilitating infections in humans and in other animals, there is a long felt need for such vaccines.

SUMMARY OF THE INVENTION

A complex of two herpesvirus glycoproteins, gH and gL, has been discovered in soluble form, which soluble complex is heretofore unknown. The complex is useful for immunizing a human against a herpesvirus infection and is therefore useful as a vaccine. The complex is also useful for determining the presence or absence of a herpesvirus infection in a human patient.

In one aspect, the invention features a preparation of a soluble herpesvirus gH/gL complex and in another aspect, the invention features a substantially pure preparation of a soluble herpesvirus gH/gL complex. Preferably, the complex is suspended in a pharmaceutically acceptable carrier. The herpesvirus is preferably selected from the group consisting of HSV-1, HSV-2, VZV, EBV, CMV, HHV-6 and HHV-7. Most preferably, the herpesvirus is HSV-1.

In a preferred embodiment, the gH component of the complex contains amino acid residues selected from the group consisting of 1-792, 1-648, 1-324 and 1-275.

In another aspect, the invention features a cell, wherein the DNA of the cell encodes a soluble herpesvirus gH/gL complex. Preferably, the cell is a HL-7 cell.

The invention further features a method of modifying a cell to render it capable of secreting a soluble herpesvirus gH/gL complex. The method involves introducing into the cell a DNA encoding a truncated form of herpesvirus gH and a herpesvirus gL molecule, wherein the gH and gL are expressed in and secreted from the cell. Preferably, the truncated form of gH contains amino acid residues selected from the group consisting of 1-792, 1-648, 1-324 and 1-275.

Also featured in the invention is a vaccine containing a soluble herpesvirus gH/gL complex suspended in a pharmaceutically acceptable carrier. In another aspect of the invention, the vaccine contains a substantially pure preparation of a soluble herpesvirus gH/gL complex suspended in a pharmaceutically acceptable carrier.

In yet another aspect, the invention features a method of immunizing a human patient against a herpesvirus infection, the method involving administering to the human a soluble herpesvirus gH/gL complex suspended in a pharmaceutically acceptable carrier. In yet another aspect the method includes a substantially pure preparation of the complex.

The invention further features a method of identifying an antiviral compound involving administering a candidate compound to a cell expressing a secreted form of a herpesvirus gH/gL complex and determining the amount of gH/gL complex secreted from the cell in the presence of the compound compared with the amount of gH/gL complex secreted from the cell in the absence of the compound, a lower amount of complex in the presence of the compound than in the absence of the compound being an indication that the compound has antiviral activity. In preferred embodiments, a plurality of compounds are administered to the cell.

By the term "substantially pure" as it refers to a gH/gL complex is meant a complex which has been substantially purified away from the components which naturally accompany it in the cell or medium in which it resides.

By the term "truncated form" as it refers to gH is meant a molecule of gH which contains less than the complete number of amino acids found in the wild type, non-mutated protein.

The file of this patent contains at least one drawing executed in color. Copies of this patent with color drawing(s) will be provided by the Patent and Trademark Office upon request and payment of the necessary fee.

BRIEF DESCRIPTION OF THE DRAWINGS

FIG. 1 is a photograph of a gel depicting analysis of carbohydrate processing in gH. Cytoplasmic extracts were prepared from HSV-1 infected L cells, or from L cells transfected with pCMV3gH-1 plus pCMV3gL-1 or with pCMV3gH-1 alone. Extracts were subsequently treated with either endo H, endo F, or were untreated and the proteins contained therein were resolved by SDS-PAGE, transferred to a nylon membrane and incubated in the presence of rabbit anti-gH serum (R82) and goat anti-rabbit horseradish peroxidase conjugate. Reacted proteins were detected using a chemiluminescent substrate. Abbreviations: gH, pCMV3gH-1; gL, pCMV3gL-1; no tx, not treated.

FIG. 2 comprising panels A and B are photomicrographs depicting analysis of folding of gH. L cells transfected with pCMV3gH-1 (A) or cotransfected with pCMV3gH-1 and pCMV3gL-1 (B) were processed for immunofluorescence and were incubated in the presence of the gH monoclonal antibody (MAb) 53S (American Type Culture Collection), which antibody reacts with correctly folded gH but does not react with incorrectly folded gH.

FIG. 3 comprising panels A and B are photomicrographs depicting intracellular localization of gH. L cells transfected with pCMV3gH-1 (A) or cotransfected with pCMV3gH-1 and pCMV3gL-1 (B) were processed for immunofluorescence and were reacted with the gH MAb 37S, an antibody capable of reacting with gH irrespective of its conformation.

FIG. 4 comprising panels A–F are photomicrographs depicting analysis of cell surface expression of gH and gL. L cells cotransfected with pCMV3gH-1 and pMMTVgL-1 were incubated in the presence (Dex+) or absence (Dex–) of 1 $\mu$M dexamethasone (Panels A and B, or panels C and D, respectively). In panels E and F, cells were cotransfected with pCMV3gH-1 and pCMV3gL-1. Expression of gH was detected using the gH MAb 37S and anti-mouse IgG fluorescein-labeled conjugate. Expression of gL was detected using rabbit anti-gL serum and anti-rabbit IgG rhodamine-labeled conjugate.

FIG. 5 comprising panels A–F are photomicrographs depicting cellular localization of gL. L cells were transfected as follows: pCMV3gL-1 alone (A and B); pCMV3gL-1 plus pCMV3gH(792) (C and D); or, pCMV3gL-1 plus pCMV3gH-1 (E and F). Expression of gL was detected using anti-gL serum and fluorescein-labeled conjugate. Cells in the panels on the left were fixed with acetone to examine internal localization of gL. Cells in the panels on the right were not fixed in order to examine cell surface expression of gL.

FIG. 6 is a photograph of a gel containing immunoprecipitated gL to determine whether gL is secreted from cells. L cells were transfected with the following plasmids: pCMV3gL-1 alone; pCMV3gL-1 plus pCMV3gH(792); or, pCMV3gL-1 plus pCMV3gH-1. Transfected cells were incubated in the presence of $^{35}$S-labeled cysteine. Supernatants were collected from cells so incubated, which supernatants were concentrated and immunoprecipitated with anti-gL serum. Immunoprecipitated proteins were resolved by SDS-PAGE. Abbreviations: gL, pCMV3gL-1; gH(792), pCMV3gH(792); gH, pCMV3gH-1.

FIG. 7 is a photograph of a gel depicting analysis of cell supernatants for the presence or absence of secreted gL and gH(792). L cells were transfected with pCMV3gL-1 plus pCMV3gH(792), or with pCMV3gH(792) alone. Transfected cells were incubated in the presence of $^{35}$S-labeled cysteine. Supernatants were collected from cells so incubated, which supernatants were concentrated and immunoprecipitated with either gH MAb R83 or with anti-gL serum. Immunoprecipitated proteins were resolved by SDS-PAGE. Abbreviations: L, pCMV3gL-1; H, pCMV3gH(792).

FIG. 8 is a photograph of a gel depicting analysis of carbohydrate processing of gL secreted by cells. L cells were transfected with pCMV3gL-1 alone or with pCMV3gL-1 plus pCMV3gH(792). Transfected cells were incubated in the presence of $^{35}$S-labeled cysteine. Supernatants were collected from cells so incubated, which supernatants were concentrated and immunoprecipitated with anti-gL serum. Immunoprecipitated proteins were treated with endo H, endo F, or were untreated and the products were resolved by SDS-PAGE. Abbreviations: L, pCMV3gL-1; H, pCMVgH(792); no tx, no treatment.

FIG. 9 is a photograph of a gel depicting analysis of complex formation between gL and various truncated mutant forms of gH. L cells were cotransfected with pCMV3gL-1 and with one of the following plasmids encoding truncated forms of gH as indicated at the top of the gel: pCMV3gH(792); pCMV3gH(648); pCMV3gH(475); and, pCMV3gH(102). Transfected cells were incubated in the presence of $^{35}$S-labeled cysteine. Supernatants were collected from cells so incubated, which supernatants were concentrated and immunoprecipitated with anti-gH serum. Immunoprecipitated proteins were resolved by SDS-PAGE.

FIG. 10 is a photograph of a gel depicting immunoprecipitation of gH/gL complex secreted by HL-7 cells. Proteins produced by HL-7 cells were labeled with $^{35}$S-cysteine, cell supernatants were obtained and were immunoprecipitated with gH MAbs 52S, 53S and LP11 as indicated at the top of the figure. As a control, proteins produced by L cells, also labeled with $^{35}$S-cysteine, were immunoprecipitated with 53S. Immunoprecipitated proteins were resolved by SDS-PAGE.

DETAILED DESCRIPTION OF PREFERRED EMBODIMENTS

Two HSV-1 specific glycoproteins, gH and gL, form a molecular complex which is present on the virion envelope. This complex is essential for viral infectivity in that it is required for entry of virus into cells and for cell to cell spread of virus which is believed to occur via membrane fusion. In the experiments described below, gH and gL have been stably expressed in and secreted from mammalian cells in culture. This complex so secreted, may be obtained in large quantities for use as a candidate vaccine for protection of individuals against infections by HSV-1, or for eliminating or diminishing the frequency of reactivation of the virus from the latent state thus, reducing the severity of recurrent infections. The complex may also be useful as a diagnostic reagent for assessing the presence or absence of a herpesvirus infection in a human. Such an assessment is made by obtaining serum from the individual and reacting it with the complex in a standard immunoassay such as radioimmunoassay or enzyme linked immunoadsorbent assay (ELISA).

Homologs of the genes encoding HSV-1 gH and gL have been identified in several other herpesviruses including human CMV (Cranage et al., 1988, J. Virol. 62:1416), VZV (Davison and Scott, 1986, J. Gen. Virol. 67:1759) and EBV (McGeoch and Davison, 1986, Nucl. Acids Res. 4:4281). The CMV UL115 gene, a positional homolog of the HSV-1 gL gene, encodes a secreted protein which forms a complex with CMV gH and is therefore a positional and likely functional (although not a sequence) homolog to HSV-1 gL (Kaye et al., 1992, J. Gen. Virol. 73:2693; Spaete et al., 1993, Virology 193:853). HHV-6 (Josephs et al., 1991, J. Virol. 65:5597), pseudorabies virus (Klupp et al., 1991, Virology 182:732) and herpesvirus saimiri (Gompels et al., 1988, J. Gen. Virol. 69:2819) also each encode homologs of HSV-1 gH.

Cells and Viruses. Mouse Ltk⁻ cells (L cells) were propagated in α-minimal essential medium (Gibco) supplemented with 10% heat-inactivated fetal calf serum (FCS, obtained from HyClone Laboratories), gentamicin, amphotericin B, vitamins, and N-2hydroxyethypiperazine-N'-2-ethanesulfonic acid (HEPES) buffer solution. HSV-1 strain NS was propagated as described (Cines et al., 1982, J. Clin. Invest. 69:123).

Antibodies. Polyclonal antibodies and MAbs used in this study were as follows: rabbit polyclonal anti-gH antibody preparations R82 and R83 (Roberts et al., 1991, Virology 184:609); anti-gH MAbs include 37S (Showalter et al., 1981, Infn. Immun. 34:684), 53S (American Type Culture Collection), and LP11 (Buckmaster et al., 1984, Virology 139:408); rabbit antiserum raised against the gL UL1-2 peptide (anti-gL serum; Hutchinson et al., 1992, J. Virol. 66:2240).

Plasmids expressing gH. Plasmid pCMV3gH-1 contains a 3.1 kb HindIII fragment obtained from pSR95 (Roberts et al., 1991, Virology 184:609), which fragment contains the entire HSV-1 strain NS gH coding region ligated into the HindII site in the polylinker of pCMV3 (Andersson et al., 1989, J. Biol. Chem. 264:8222). Thus, plasmid pCMV3gH-1 encodes gH under the control of the human cytomegalovirus immediate early promoter. A second plasmid, pCMV3gH (792) encodes gH-1(792) which is a truncated form of the wild type protein terminating at amino acid 792 and was constructed by insertion of an SpeI linker containing termination codons within the gH coding region as described by Roberts et al. (1991, Virology 184:609).

Plasmids expressing gL. The UL1 open reading frame which encodes gL (McGeoch et al., 1988, J. Virol. 62:1486) was amplified from viral DNA using the polymerase chain reaction (PCR). The following synthetic oligonucleotide primers containing the underlined XbaI restriction enzyme sites were designed to facilitate cloning:

5'-TGCTCTAGAGCGCTATGGGGATTTTGGGT-3' (upstream primer) and 5'-TGCTCTAGAGGTTTCCGTCGAGGCATCGT-3' (downstream primer) [SEQ. ID. NOS; 1 and 2, respectively]. To prepare the template for amplification, approximately $10^5$ HSV-1 virions were lysed by heating to 95° C. for 10 minutes. The lysate was added to a 100 µl PCR reaction mixture containing 2.5 units of TaqI DNA polymerase (Perkin Elmer, Cetus), 10 mM Tris-HCl (pH 8.3), 50 mM KCl, 1.5 mM $MgCl_2$, 0.001% gelatin (wt/vol), the four deoxyribonucleotides each at a concentration of 200 µM, and 1.0 µM of each of the primers. The PCR mixture was subjected to 35 cycles of amplification (94° C. for 1 minute, 55° C. for 1 minute, and 72° C. for 1.5 minutes). The product, a 718 bp fragment was digested with XbaI in order to generate cohesive termini and was then gel purified and ligated into the XbaI sites of both pCMV3 (Andersson et al., 1989, J. Biol. Chem. 264:8222) and pMMTV (Friedman et al., 1989, Mol. Cell. Biol. 9:2303) generating the plasmids pCMV3gL-1 and pMMTVgL-1, respectively. Transcription of the gL gene is thus under the control of the CMV immediate early promoter in pCMV3gL-1 and under the control of the inducible dexamethasone mouse mammary tumor virus promoter in pMMTVgL-1.

Transfection of cells. Transient transfections were performed using calcium phosphate (Graham and van der Eb, 1973, Virology 52:456). In co-transfection assays, 4 µg/well of plasmid was used; for single plasmid transfections, 8 µg/well was used. At 42 hours post-transfection, cell supernatants were collected and assayed by immunoprecipitation and/or cells were harvested for immunofluorescence studies.

Immunoprecipitation and gel electrophoresis of proteins. At 18 hours post-transfection, L cells transfected with plasmid DNA as described above were washed twice in Dulbecco's modified Eagle medium lacking cysteine (DMEM/cys-; Gibco BRL). The cells were incubated in DMEM/cys-supplemented with 200 µCi per well of $^{35}$S-cysteine and 10% FCS for 24 hours. Cell supernatants were collected, centrifuged to remove any non-adherent cells and concentrated 10-fold by centrifugation at 5520×g for 1 hour in Centricon-10 concentrator tubes (Amicon, Inc.). Concentrated supernatants were treated with 1 mM each of Nα-p-tosyl-L-lysine chloromethyl ketone (TLCK) and N-tosyl-L-phenylalanine chloromethyl ketone (TPCK) and were stored at −20° C. For immunoprecipitation, supernatants were thawed and mixed with a buffer containing 10 mM Tris-HCl, pH 8.0, 100 mM NaCl, 1 mM EDTA. 0.5% Noniodet P-40 (wt/vol), and 0.25% gelatin (wt/vol). Supernatants were incubated with 3 µl of either R83 or anti-gL serum and PANSORBIN *Staphylococcus aureus* cells (CalBiochem). Following precipitation, immunoprecipitates were washed three times in high salt buffer (10 mM phosphate buffer, pH 7.2, containing 0.65M NaCl, 1 mM EDTA, 1% Triton X-100) and once in low salt buffer (10 mM phosphate buffer, pH 7.2, containing 0.15M NaCl, 1 mM EDTA, 1 Triton X-100). The immunoprecipitates were then solubilized in dissolution buffer (100 Tris HCl, pH 6.8, 4% SDS, 0.2% bromophenol blue, 20% glycerol and 10% β-mercaptoethanol), and the proteins were resolved by SDS-PAGE under denaturing conditions as described (Cohen et al., 1986, J. Virol. 60:157). Proteins in the gel were fixed in a mixture of glacial acetic acid and methanol, the gel was impregnated with Autofluor (National Diagnostics) and was exposed to X-ray film at −70° C.

Enzymatic treatment of cytoplasmic extracts and immunoprecipitates. Cytoplasmic extracts were prepared from infected or transfected cells as described (Cohen et al., 1986, J. Virol. 60:157). Extracts were treated with 5 mU of endo-β-N-acetylglucosaminidase (endo H; Boehringer Mannheim Biochemicals) or 250 mU of endoglycosidase F/N-glycosidase F (endo F; Boehringer Mannheim Biochemicals) for 2 hours at 37° C. Immunoprecipitates were eluted from PANSORBIN cells by boiling in buffer containing 0.1M sodium phosphate (pH 7.5), 0.5% β-mercaptoethanol and 0.1% SDS, and were diluted 2-fold in 0.1 M sodium phosphate buffer containing 1% octyl glucoside, 150 µM phenanthroline and 10 mM EDTA. Samples were then treated for 2 hours at 37° C. with 5 mU of endo H or 250 mU of endo F.

Western blot analysis. Following enzymatic treatment of cytoplasmic extracts, proteins were resolved by SDS-PAGE under denaturing conditions and transferred to a nylon membrane which was incubated in the presence of R82. Bound antibody was detected using goat anti-rabbit horseradish peroxidase conjugate (Boehringer Mannheim Biochemicals) and a chemiluminesccent substrate solution (New England Nuclear). The membrane was exposed at room temperature to Kodak X ray film.

Immunofluorescence. To examine expression of gH and gL on the cell surface, cells transfected with plasmids expressing either protein were suspended in phosphatebuffered saline (PBS) containing 0.005M EDTA, washed by centrifugation and resuspended in PBS containing 1% bovine serum albumin (BSA). The cells were incubated at 4° C. for 30 minutes in the presence of gH MAb alone, anti-gL-1 serum alone, or in the presence of both antibodies (for double label immunofluorescence studies). The cells were washed and further incubated in the presence of goat anti-mouse IgG F(ab')$_2$ fluorescein-labeled conjugate (to detect gH) and/or goat anti-rabbit IgG F(ab')$_2$ fluorescein-labeled or rhodamine-labeled conjugate (to detect gL). Cells so stained were visualized using a Leitz epifluorescence microscope. For double-label fluorescence studies, the same microscopic fields were viewed under fluorescein and rhodamine filters.

Additional immunofluorescence studies were performed on acetone fixed cells. Transfected cells suspended in PBS containing 1% BSA were allowed to adhere to glass microscope slides and were fixed in acetone prior to incubation in the presence of antibody and conjugate as described above.

Figure 1:
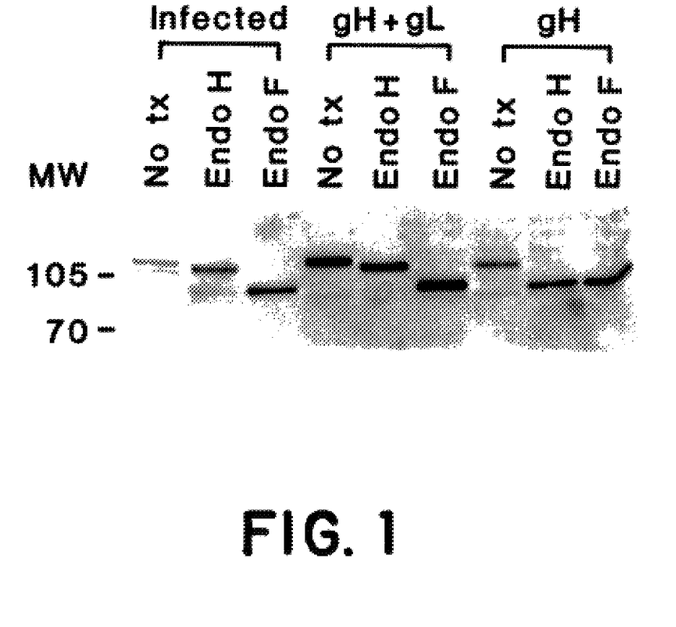

Requirement of gL for normal processing of gH in transfected cells. Normal processing of gH requires addition of N-linked carbohydrates to the nascent molecule (Buckmaster et al., 1984, Virology 139:408). However, in the absence of other HSV-1 glycoproteins, processing of gH is incomplete. In order to establish a definitive role for gL in processing of gH, gH produced in the presence or absence of gL was analyzed for sensitivity to endo H or endo F. Treatment of incompletely processed glycoproteins with either enzyme results in cleavage of the carbohydrate moiety and a subsequent reduction in the molecular weight of the glycoprotein compared with the completely processed glycoprotein. Glycoproteins which contain complex, fully processed carbohydrate moieties are resistant to cleavage by endo H, but remain sensitive to endo F. Cytoplasmic extracts were prepared from cells which were either infected with HSV-1 or were cotransfected with pCMV3gH-1 and pCMV3gL-1, or simply transfected with pCMV3gH-1 alone, which extracts were either subsequently untreated or were incubated in the presence of endo H and endo F. It is evident from the data presented in FIG. 1 that gH exhibits sensitivity to both endo H and endo F when expressed in the absence of gL. In contrast, when gL is present either during infection or during cotransfection, the molecular weight of gH following endo H treatment is essentially unchanged indicating that gL is required for complete processing of gH in transfected cells.

Figure 2:
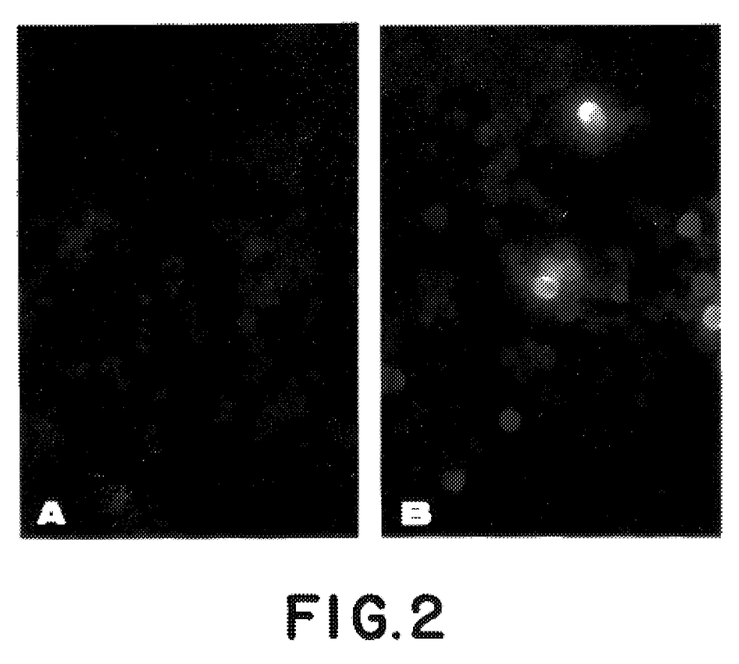

Expression of gL is required for correct folding of gH. To determine whether gH is folded correctly in gL-negative cells, reactivity of gH with the conformation-dependent gH-MAb, 53S, was examined by immunofluorescence. Extracts of L cells transfected with pCMV3gH-1 did not react with 53S (FIG. 2A), whereas extracts of cells transfected with both pCMV3gH-1 and pCMV3gL-1 exhibited strong reactivity (FIG. 2B). Similar results were observed using LP11, a gH MAb which reacts with a distinct conformational phenotype of gH (Gompels et al., 1991, J. Virol. 65:2393). These results indicate that, in transfected cells, folding of gH is normal in the presence of gL but is abnormal in the absence of gL.

Figure 3:
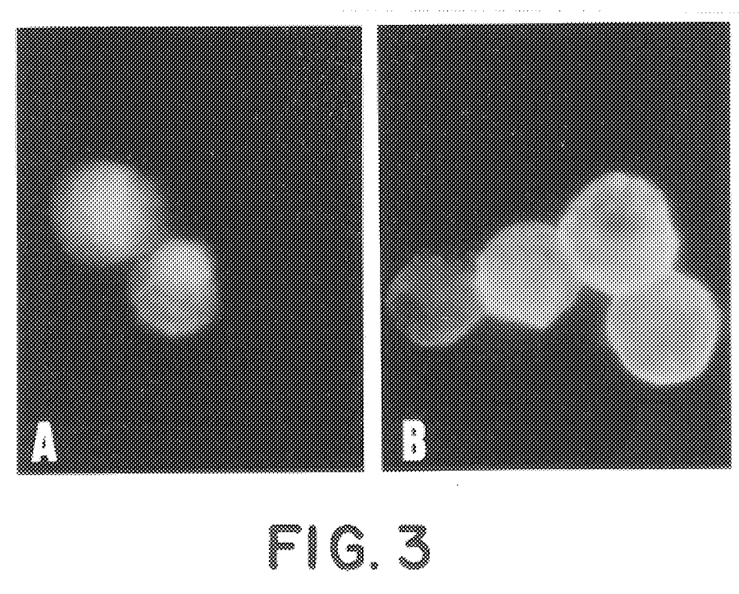
Figure 4:
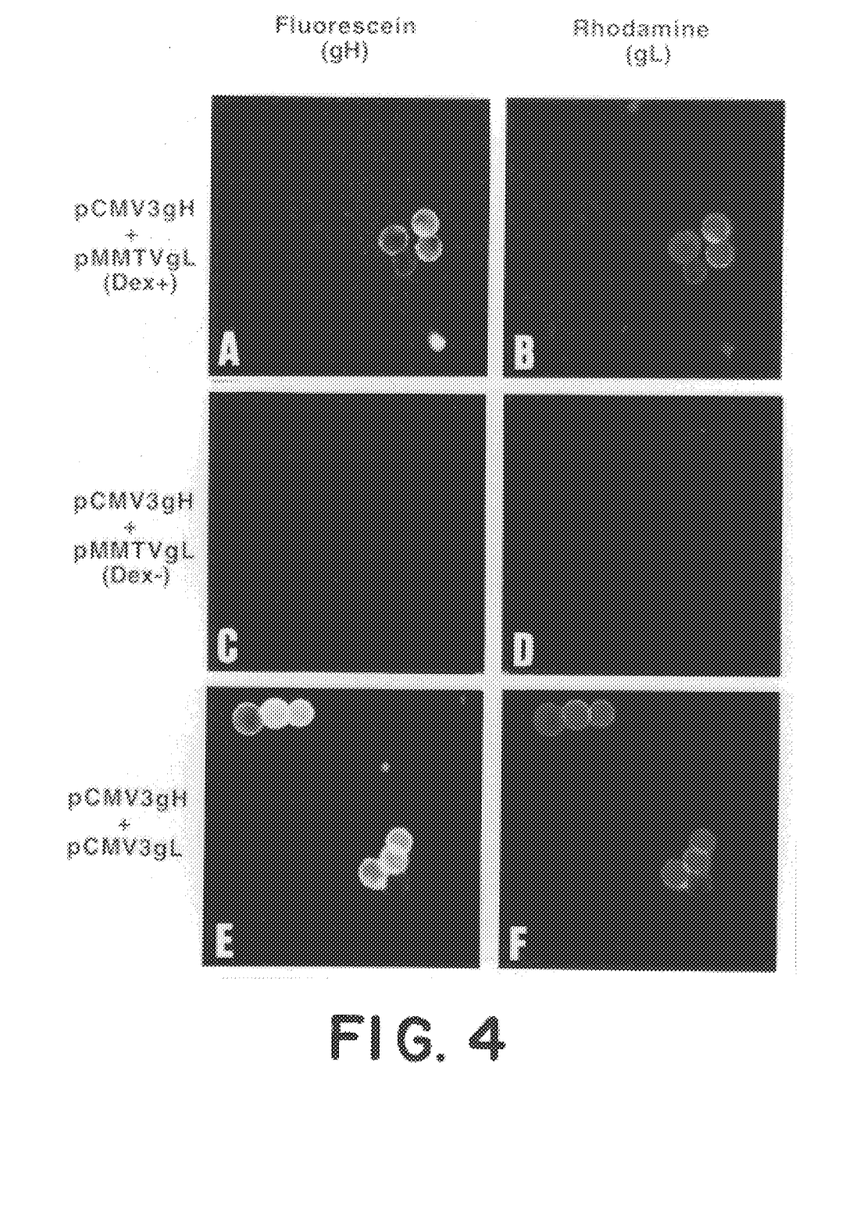

Expression of gL is required for intracellular transport and cell surface expression of gH in transfected cells. To examine the effect of expression of gL on intracellular transport and cell surface expression of gH, L cells were transfected with pCMV3gH-1 either alone or in combination with pCMV3gL-1. The intracellular localization of gH in cells so transfected was assessed by immunofluorescence using the MAb 37S, a MAb which binds to gH irrespective of its structural conformation (Roberts et al., 1991, Virology 184:609). In the absence of gL, the intracellular distribution of gH was cytoplasmic and included some perinuclear localization suggesting retention of this glycoprotein in the endoplasmic reticulum (FIG. 3A). However, in the presence of gL, gH was distributed throughout the cell in a uniform manner with some localization at the cell perimeter suggesting cell surface expression (FIG. 3B). To examine cells surface expression in more detail, these studies were repeated using unfixed cells. In this instance, gL was expressed from the dexamethasone-inducible plasmid pMMTVgL-1. Thus, cells were cotransfected with pCMV3gH-1 and pMMTVgL-1 and were subsequently incubated either in the presence or absence of dexamethasone. Cells so transfected were treated with the gH MAb 37S, and with anti-gL serum, and were then stained with fluorescein-labeled conjugate (to detect gH) and rhodamine-labeled conjugate (to detect gL). In cells incubated in the presence of dexamethasone, both gH and gL co-localized to the cell surface (FIG. 4, A and B). This was also true when cells were cotransfected with pCMV3gH-1 and pCMV3gL-1 (FIG. 4, E and F). However, in the absence of dexamethasone, neither glycoprotein was found at the cell surface. Thus, gL is required for intracellular processing of gH.

Figure 5:
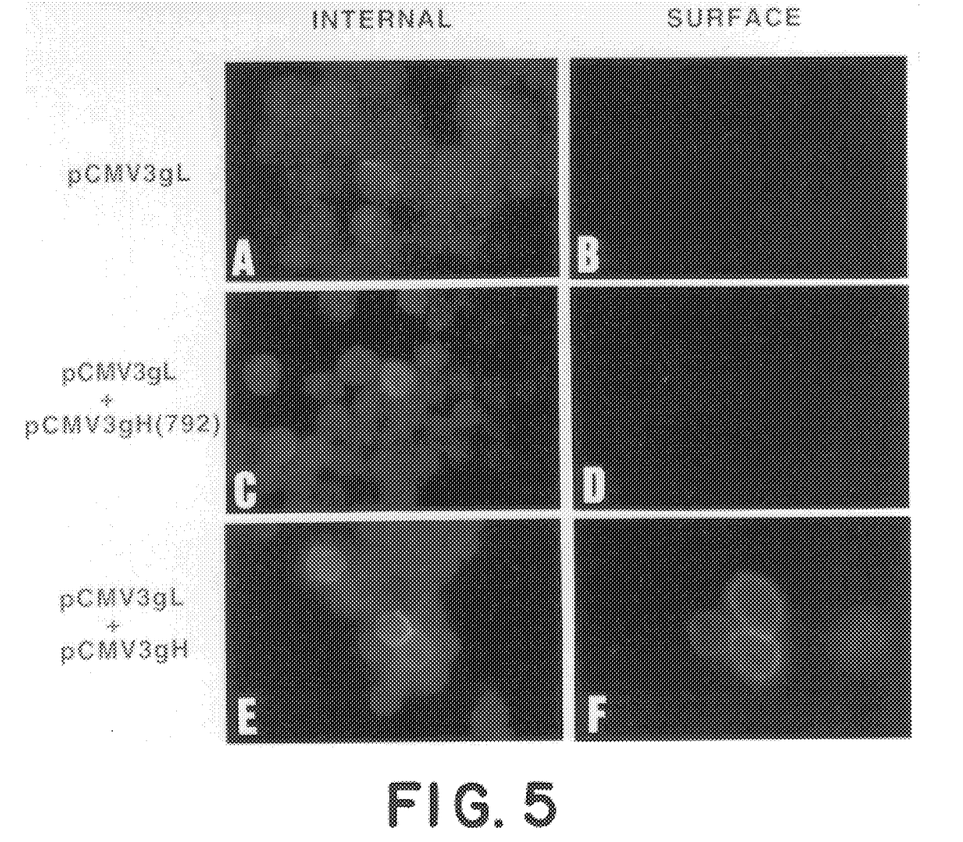

Membrane association of gL results from its association with gH. The predicted amino acid sequence of gL suggests that it is a secreted rather than a membrane associated glycoprotein (McGeoch et al., 1988, J. Gen. Virol. 69:1531). To investigate whether gL is capable of independent association with the cell membrane (i.e., in the absence of membrane association by gH), gL was co-expressed with a mutant of gH, which mutant lacks the membrane spanning domain of the glycoprotein (gH792). In cells transfected with a plasmid encoding gL, or with a plasmid encoding gL and the truncated form of gH, gL was not detected on the cell surface (FIG. 5, B and D); however, in cells transfected with plasmids encoding gL and full length wild type gH, gL was detected on the cell surface (FIG. 5, F). That gL was actually expressed in each of these sets of transfected cells was confirmed by immunofluorescence of permeabilized cells (FIG. 5, A, C and E). These data demonstrate that cell surface expression of gL is dependent upon expression of wild type gH.

Figure 6:
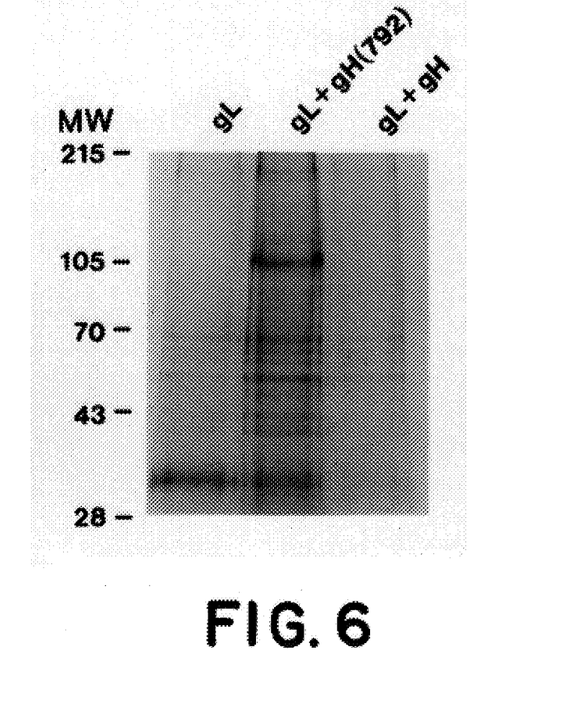
Figure 7:
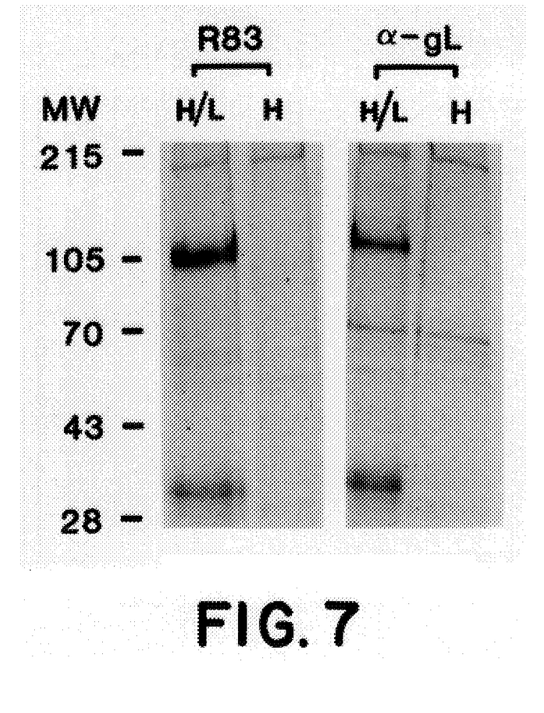

Secretion of gL. To examine secretion of gL from transfected cells, cells were transfected with the following combinations of plasmids: pCMV3gL-1 alone; pCMV3gL-1 plus pCMV3gH(792); or, pCMV3gL-1 plus pCMV3gH-1. In each instance, proteins synthesized by these cells were labeled with $^{35}$-cysteine, they were extracted from the cell supernatants and were analyzed by immunoprecipitation using anti-gL serum. A 30 kDa protein (gL) was identified in supernatants from cells transfected with pCMV3gL-1 alone and in cells transfected with pCMV3gL-1 plus pCMV3gH (792). This protein was not identified in supernatants from cells cotransfected with pCMV3gL-1 and pCMV3gH-1 (FIG. 6). A protein of 105 kDa in size was also immunoprecipitated by anti-gL serum and by R83 (anti-gH MAb) in cells cotransfected pCMV3gL-1 plus pCMV3gH(792) suggesting that both gL and the truncated form of gH are secreted from these cells as a complex (FIGS. 6 and 7). Neither the 30 nor the 105 kDa proteins were evident in supernatants from cells transfected with pCMV3gH(792) alone. Thus, these experiments demonstrate that gL and gH are capable of forming a complex at the cell surface and that gL does not independently associate with the cell membrane, rather, its association with this membrane is dependent upon the presence of the membrane anchor portion of gH. The finding that gL is secreted from cells independent of gH was unexpected since previous studies suggested that processing of gL required the presence of gH (Hutchinson et al., 1992, J. Virol. 66:2240).

Figure 8:
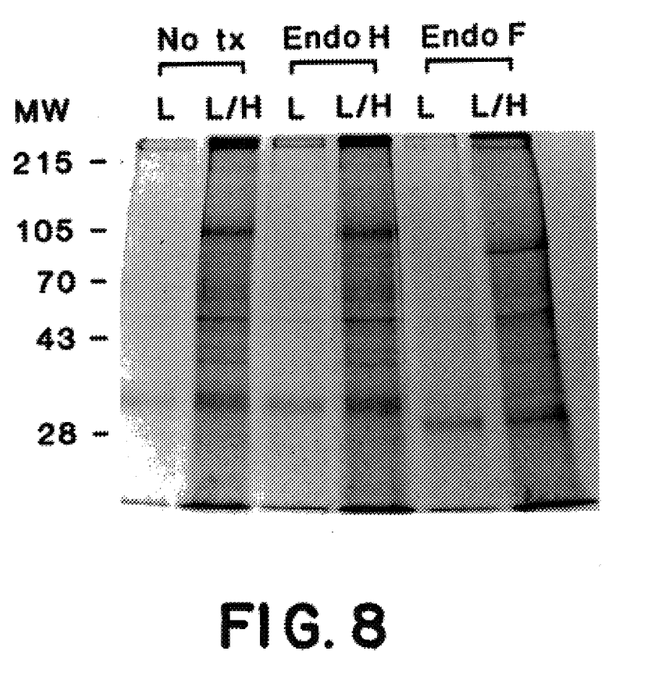

Confirmation that gH is not required for processing of the carbohydrate moiety of gL. To further investigate the role of gH in processing of gL, cells were transfected with either pCMV3gL-1 alone or were cotransfected with pCMV3gL-1 and pCMV3gH(792) . Supernatants were collected from cells so transfected and any gL present therein was examined for sensitivity to either endo H or endo F. The same pattern of enzyme sensitivity was evident irrespective of the presence or absence of gH (FIG. 8). Therefore, gH is not required for either the addition or processing of N-linked carbohydrates on gL expressed in transfected cells.

Figure 9:
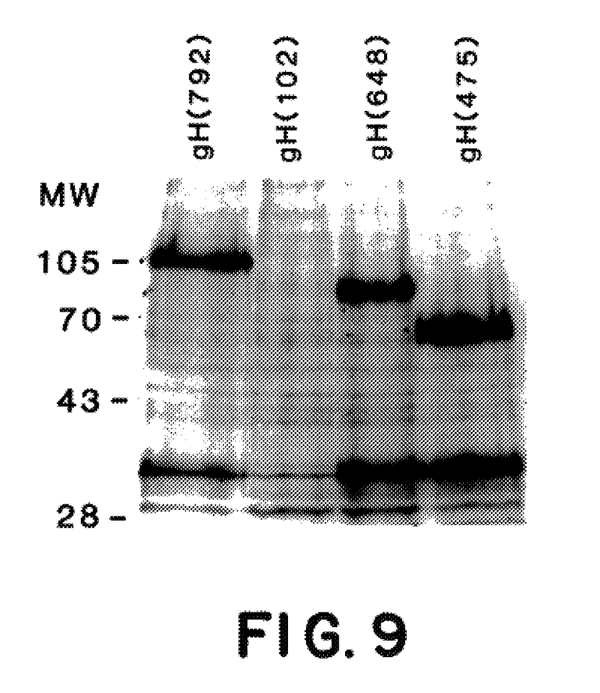

The region of gH required for complex formation with gL. As described above, coexpression of gL with the truncated form of gH [gH(792)] results in a complex comprising the two proteins, which complex is secreted from cells. To determine which domains of gH are required for complex formation, additional mutants of gH, expressing further truncated forms of this glycoprotein, were tested in the transfection assay described above. The mutants tested were as follows: gH(648), gH(475), and gH(102), each of which expresses a protein of 648, 475 and 102 amino acids in length. The plasmids encoding these mutated forms of gH are designated pSR124 (648), pSR123 (475) and pSR125 (102). Each plasmid encodes the truncated form of gH under the control of the Rous sarcoma virus promoter (Roberts et al., 1991, Virology 184:609). Cells were cotransfected with pCMV3gL-1 and with one of the mutant plasmids described above and were incubated in medium containing $^{35}$S-cysteine. At 18 hours post-transfection, cell supernatants were harvested and the proteins contained therein were immunoprecipitated with anti-gH serum as described above. Immunoprecipitates were resolved by SDS PAGE and the results are shown in FIG. 9. Mutant forms of gH which terminate at amino acid residues 792, 648 and 475 were secreted from cotransfected cells in a complex with gL. However, when a mutant encoding only 102 amino acid residues of gH was used, a gH/gL complex was not detected in cell supernatants. Additional experiments have been conducted in a similar manner to that described above and it is now believed that a region of gH comprising amino acids 1-324 and a region comprising amino acids 1-275 are capable of forming a complex with gL. Thus, the region of gH required for interaction with gL resides in the amino-terminal portion of the molecule between residues 1-275. As noted above, the membrane anchor region of gH resides in the carboxy terminus of the molecule between amino acid residue 792 and the last amino acid residue at the carboxy terminus.

Construction of a stable gH/gL expressing cell line.

For the purposes of vaccine production, generation of a gH/gL complex in the cell lines described below has significant advantages over other methods of production of this complex which methods may involve for example, extraction of a gH/gL complex from infected cells. In the latter case, since wild type gH comprises a hydrophobic membrane anchor region, it is necessary to use detergents during extraction to remove the membrane portion. Such treatment may in fact alter the conformation of the complex and thereby alter its immunogenic properties. By using the cell lines described below, a secreted form of gH is produced as a complex with gL and thus, further extraction and purification prior to use as a vaccine is minimized. In addition, the use of mammalian cells is advantageous in that both insect and lower eukaryotic cells each process carbohydrates somewhat differently than do mammalian cells. Thus, the use of mammalian cells ensures correct processing of the components of the complex and thereby ensuring preservation of the immunologically protective epitopes within the complex.

Cell lines which constitutively express and secrete gH/gL as a complex were constructed as follows. L cells were cotransfected with pCMVgH(792) and pCMVgL-1 and with the plasmid pX343 which encodes a gene conferring resistance of cells to hygromycin B (Blochlinger et al., 1984, Mol. Cell. Biol. 4:2929). Cells so transfected were incubated in the presence of hygromycin B (200 μg/ml). Twenty four clones of hygromycin B resistant cells were selected and supernatants therefrom were first screened for production of gH by Western blot analysis. Of these, two clones were further tested for production of both gH and gL by immunoprecipitation. Both of these clones expressed and secreted the gH/gL complex. One of these clones, designated HL-7, produced large amounts of the complex and was therefore selected for additional studies.

Figure 10:
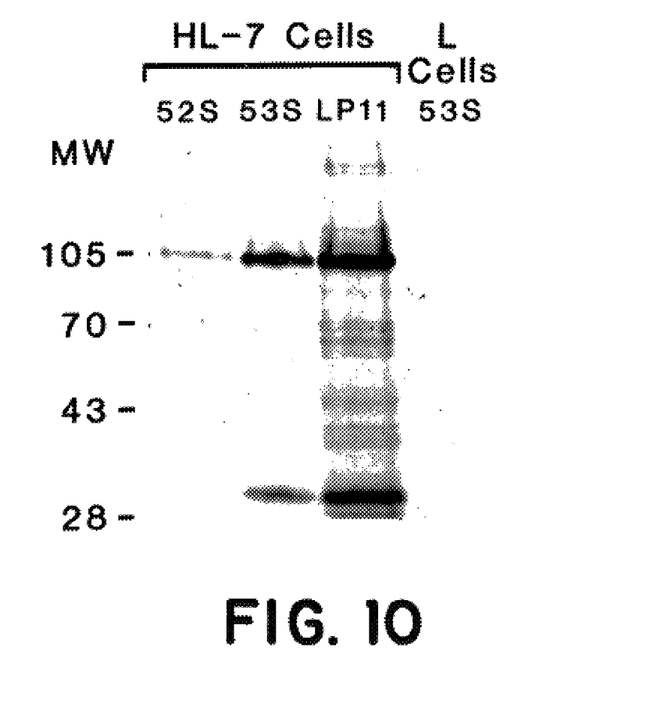

The gH/gL complex secreted by HL-7 cells was found to be immunoprecipitable by gH MAbs 52S, 53S, and LP11 (FIG. 10). Since these MAbs are dependent upon correct folding of gH in that they react with distinct structural epitopes on the molecule, the gH/gL complex secreted by HL-7 cells appears to have a structure similar to that of the wild type complex.

Purification of gH/gL complex from HL-7 cells. Preparations of gH/gL complex secreted from HL-7 cells were purified by immunoaffinity chromatography using the gH-specific MAb, 53S as follows. The MAb was purified from mouse ascites using a protein A agarose column and was then covalently linked to a cyanogen bromide-activated Sepharose 4B immunoadsorbant column at a concentration of approximately 4 mg of IgG per ml of packed Sepharose. To purify the gH/gL complex (i) HL-7 supernatant was passed over the 53S affinity column to absorb the complex; (ii) the column was washed with Tris-HCl, pH 8.0; (iii) adsorbed proteins were eluted from the column in fractions using a 50 mM glycine buffer (pH 2.5) containing 0.5 M NaCl and 0.1% Triton X-100; (iv) fractions so eluted were immediately neutralized with Tris-HCl, pH 9.0; (v) fractions were analyzed by SDS-PAGE and proteins were visualized by silver staining to identify the gH/gL complex; and, (iv) fractions which contained the complex were pooled and concentrated approximately 20-fold in Centricon-10 concentrator tubes.

Figure 11:
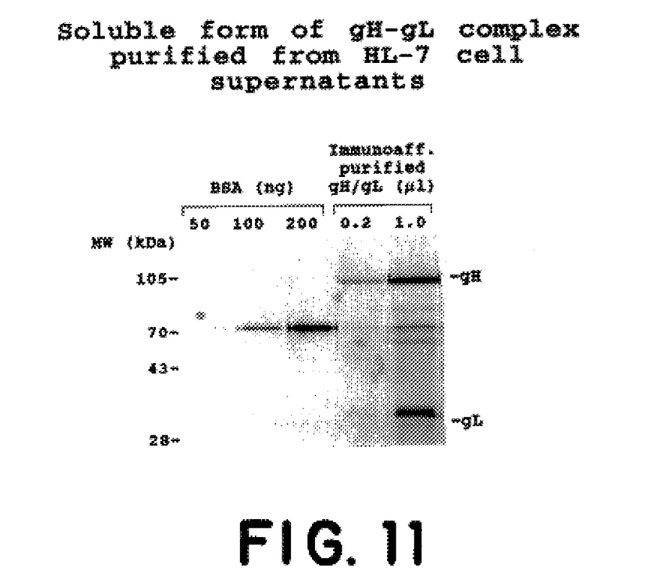
FIG. 11 is a photograph of an SDS-PAGE depicting immunoaffinity purification of gH/gL complex secreted from HL-7 cells. Lanes 1–3, 50 nanograms, 100 nanograms and 200 nanograms of bovine serum albumin, respectively; lanes 4 and 5, 0.2 $\mu$l and 1.0 $\mu$l of pooled and concentrated 53S immunoaffinity column purified gH/gL complex, respectively.

To quantitate the amount of complex obtained in the concentrated samples, the intensity of staining of the gH and gL bands on SDS-PAGE was compared with known quantities of protein standard (bovine serum albumin). These data are presented in FIG. 11. It is estimated that each sample contained approximately 0.5 μg/gl of gH/gL complex. It is possible to purify 0.5 mg of gH/gL complex from approximately 1 liter of HL-7 supernatant using the procedures described herein. Further, densitometric analysis of the silver stained gel indicates that gH and gL are present in the complex at a purity of approximately 90%. In addition, approximately 50% of the gH/gL complex secreted from HL-7 cells possess a conformation which is indistinguishable from that of the native molecule as assessed by binding to the 53S MAb.

Identification of a putative membrane fusion region of gH. A computer-based analysis of the amino acid sequence of gH was performed and revealed a region of the protein predicted to form an amphophilic α-helix extending from approximately amino acid residues 280–310, which helix is indicative of a membrane fusion region in influenza virus (White, 1992, Science 258:917). A gH expression plasmid (derived from pCMV3gH-l) was constructed wherein amino acid residues 275–324 were deleted (i.e., the deleted amino acid residues encompass the putative membrane fusion region) and a linker encoding 5 amino acids was inserted at the site of the deletion to re-establish the correct reading frame. The resulting gH mutant, pCMVgHΔ(275–324), encodes a protein which folds correctly and is transported to the cell surface when expressed in cells also expressing wild type gL. Furthermore, this deleted gH retains the ability to form a complex with gL as assessed in the co-immunoprecipitation assay described above. The ability of the deleted gH to rescue a gH negative virus was determined in a complementation assay as follows. L cells were transiently transfected with pCMVgH-1 or pCMVgHΔ (275–324), or were mock transfected. At 18 hours post-transfection, cells were infected with a gH negative mutant virus and incubation was continued for an additional 24 hours. The amount of virus produced was then assessed by plaque assay. Cells transfected with pCMVgH-1 produced $2.5 \times 10^5$ infectious virus per ml while mock transfected cells produced less than $1.5 \times 10^2$ virus per ml. Cells which were transfected with pCMVgHΔ(275–324) also produced negligible amounts of infectious virus i.e., less than $1.5 \times 10^2$ virus per ml, indicating that this plasmid was incapable of rescuing the gH negative phenotype exhibited by the gH negative virus. Thus, deletion of gH in the region of amino acid residues 275–324 renders the protein non-functional.

Additional gH/gL complexes. Based upon the experiments described herein, it is well within the skill of those in the art to take plasmids encoding HSV-1 truncated gH and full length gL and introduce them into a mammalian cell such that the cells become stably transfected with these plasmids and are caused to express and secrete a soluble form of gH/gL complex as described herein. It is also well within the skill of those in the art to take yet other plasmids encoding gH and gL (i.e., DNA obtained from other strains of HSV-1 or various strains of HSV-2, VZV, EBV, CMV, HHV-6 or HHV-7, which DNA encodes gH and gL) and generate cell lines which secrete soluble gH/gL complex following the teaching contained herein. Further, the invention should not be construed to be limited to the particular method of introduction of herpesvirus DNA into mammalian cells described herein. Rather, other methods may be used to generate cells which express a soluble form of gH/gL complex. Such methods include, but are not limited to, the use of retroviral and other viral vectors for delivery of herpesvirus-specific gH/gL encoding DNA into cells and the use of other chemical means of transfection. In addition, the complex to be formed by cells encoding gH/gL may include a mixture of gH derived from one virus strain and gL derived from yet another virus strain. Generation of such mixed complexes is accomplished using the protocols described above and other protocols available to virologists, described for example in Sambrook et al. (1989, Molecular Cloning: A Laboratory Manual, Cold Spring Harbor, N.Y.).

Immunization of Mice with gH/gL. It has been possible to generate antibodies against the gH/gL complex in a mouse. A Balb/c mouse was immunized at biweekly intervals with 5 doses of approximately 10 μg of gH/gL per dose. Serum obtained from the mouse post-immunization contained a high titer of antibody which reacted with the complex in an ELISA. Thus, the purified complex is immunogenic in mice with regard to the humoral immune response. It is likely that a cellular immune response to the gH/gL complex may also play a role in the protective response to this complex.

To determine the efficacy of the gH/gL complex as a vaccine, HL-7 cell secreted gH/gL complex is administered intraperitoneally to mice using the Ribi adjuvant system (RAS; Ribi Immunochemical Research, Hamilton, Mont.), or other suitable adjuvant. Both pre- and post-immune serum is obtained from the mice and the presence or absence of antibodies is determined in the standard assays described herein. The ability of anti-gH or gL antibodies to neutralize HSV is determined in a standard viral neutralization assay, such as but not limited to, a plaque reduction neutralization assay. Mice are administered a range of concentrations of gH/gL complex from 0.1 to 20 μg per dose, using several different immunization schedules, i.e., weekly, biweekly, in order to determine the optimum conditions for effective immunization of the mice against HSV. Sera obtained from mice so immunized are tested for the ability to neutralize HSV-1 strain NS (that strain from which the complex is derived) and other strains of both HSV-1 and HSV-2 in addition to other herpesviruses such as VZV, CMV, EBV, HHV-6 and HHV-7. Since the ability of an antibody to neutralize virus in culture is predictive of the protective activity of that antibody, neutralization of any one of the viruses listed above by antibody raised against HL-7 cell secreted gH/gL is predictive of the ability of gH/gL complex to serve as a subunit vaccine candidate against that virus.

To assess whether antibody raised against gH/gL protects mice against in vivo challenge with virus, immunized and non-immunized mice are administered various concentrations of virus intraperitoneally at a time post-immunization when peak antibody levels are apparent following the experiments described above. The number of immunized animals which survive challenge by virus is indicative of the efficacy of the gH/gL complex as a vaccine candidate. Although these studies will be initially conducted using an intraperitoneal route, subsequent studies will involve all possible routes of administration including, but not limited to, intramuscular, subcutaneous and even oral routes of administration. In addition, these studies will be expanded to include other animal models for herpesvirus infections, such as guinea pigs. Furthermore, studies may be conducted to examine viral latency in gH/gL immunized animals surviving virus challenge. Such studies will be performed according to published protocols, such as that described by Stanberry (Pathogenesis of herpes simplex virus infection and animal models for its study. In: Current Topics in Microbiology and Immunology, 179: Herpes simplex virus: Pathogenesis and Control, Springer Verlag (Berlin), 1992, pp 15–30).

Administration to humans. The gH/gL complex is administered to a human either subcutaneously, intramuscularly, orally, intravenously, intradermally, intranasally or intravaginally, The complex is first suspended in a pharmaceutically acceptable carrier which is suitable for the chosen route of administration and which will be readily apparent to those skilled in the art of vaccine preparation and administration. The dose of vaccine to be used may vary dependent upon any number of factors including the age of the individual and the route of administration. Typically, the gH/gL complex is administered in a range of 1 μg to 50 mg of protein per dose. Approximately 1–10 doses are administered to the individual at intervals ranging from once per week to once every few years.

While this invention has been disclosed with reference to specific embodiments, it is apparent that other embodiments and variations of this invention may be devised by others skilled in the art without departing from the true spirit of the invention. The appended claims are intended to be construed to include all such embodiments and equivalent variations.

---

---

What is claimed:

1. A substantially pure preparation of a soluble herpes simplex virus type 1 gH/gL complex suspended in a pharmaceutically acceptable carrier, wherein said complex is capable of eliciting herpes simplex virus neutralizing antibody when inoculated into an animal, and further wherein said gH is a truncated form comprising amino acid residues selected from the group consisting of 1-792, 1-648, 1-475, 1-324 and 1-275.

2. A cell, the DNA of said cell encoding a soluble herpes simplex virus type 1 gH/gL complex capable of eliciting herpes simplex virus neutralizing antibody when inoculated into an animal, wherein said gH is a truncated form comprising amino acid residues selected from the group consisting of 1-792 1-648, 1-475, 1-324 and 1-275.

3. The cell of claim 2, wherein said cell is HL-7.

4. A method of modifying a cell to render it capable of secreting a soluble herpes simplex virus type 1 gH/gL complex, wherein said complex is capable of eliciting herpes simplex virus type 1 neutralizing antibody when inoculated into an animal, comprising introducing into said cell DNA encoding a truncated form of herpes simplex virus type 1 gH comprising amino acid residues selected from the group consisting of 1-792, 1-648, 1-475, 1-324 and 1-275 and full length herpes simplex virus type 1 gL, wherein said gH and said gL are expressed in and secreted from said cell.

* * * * *